(12) United States Patent
Abrahamsson et al.

(10) Patent No.: US 11,707,212 B2
(45) Date of Patent: Jul. 25, 2023

(54) MICRODIALYSIS DEVICE COMPRISING ATTACHMENT SHEET

(71) Applicant: Senzime AB (publ.), Uppsala (SE)

(72) Inventors: Pernilla Abrahamsson, Umeå (SE); Robert Herz, Plauen (DE); Einar Pontén, Söderåkra (SE); Bjoern Glaesel, Kirchenlamitz (DE)

(73) Assignee: SENZIME AB (PUBL.), Uppsala (SE)

( * ) Notice: Subject to any disclaimer, the term of this patent is extended or adjusted under 35 U.S.C. 154(b) by 259 days.

(21) Appl. No.: 17/145,078

(22) Filed: Jan. 8, 2021

(65) Prior Publication Data

US 2021/0145326 A1 May 20, 2021

Related U.S. Application Data

(63) Continuation of application No. 15/755,526, filed as application No. PCT/EP2016/070634 on Sep. 1, 2016, now Pat. No. 10,966,641.

(30) Foreign Application Priority Data

Sep. 4, 2015 (SE) .................................. 1551133-0

(51) Int. Cl.
*A61B 5/145* (2006.01)
*A61B 5/00* (2006.01)
(Continued)

(52) U.S. Cl.
CPC .......... *A61B 5/14528* (2013.01); *A61B 5/688* (2013.01); *A61M 25/02* (2013.01);
(Continued)

(58) Field of Classification Search
CPC ... A61B 5/14528; A61B 5/688; A61B 5/6852; A61B 5/14525; A61M 25/02;
(Continued)

(56) References Cited

U.S. PATENT DOCUMENTS 5,607,390 A   3/1997   Patsalos et al.
6,478,767 B1  11/2002  O'Connell
(Continued)

FOREIGN PATENT DOCUMENTS

WO   WO 2009/095020   8/2009
WO   WO 2010/061680   6/2010

OTHER PUBLICATIONS

Abrahamsson et al., "Methodological aspects on microdialysis sampling and measurements", 2010, pp. 1-59, NRL: https://www.diva-portal.org/smash/get/diva2:360737/FULLTEXT01.pdf.

*Primary Examiner* — Laura A Bouchelle
*Assistant Examiner* — John A Doubrava
(74) *Attorney, Agent, or Firm* — James S. Keddie; Bozicevic, Field & Francis LLP

(57) ABSTRACT

The present disclosure relates to a dialysis device (1), more particularly a microdialysis device for the sampling of substances from the surface of a body organ. The device is particularly useful in the context of the monitoring of a moving organ, such as a beating heart, as the device comprises attachment means (2) allowing for a flexible and reliable attachment thereto. Furthermore, the microdialysis device provides for an efficient exchange of substances, such as metabolic substances, between the organ and the dialysis fluid through a semi-permeable material forming part of the device. There is also provided a method encompassing the device of the disclosure.

16 Claims, 7 Drawing Sheets

(51) Int. Cl.
*A61M 25/02* (2006.01)
*A61M 1/16* (2006.01)

(52) U.S. Cl.
CPC .......... *A61B 5/6852* (2013.01); *A61M 1/1678* (2013.01); *A61M 2209/088* (2013.01)

(58) Field of Classification Search
CPC ........ A61M 1/1678; A61M 2025/0253; A61M 2025/0266
See application file for complete search history.

(56) References Cited

U.S. PATENT DOCUMENTS

| | | |
|---|---|---|
| 2002/0082490 A1 | 6/2002 | Roeper et al. |
| 2010/0016779 A1 | 1/2010 | O'Connell et al. |
| 2010/0113975 A1* | 5/2010 | Kuennecke ............ A61B 5/686 |
| | | 600/573 |
| 2010/0152555 A1 | 6/2010 | Abrahamsson |
| 2015/0025436 A1* | 1/2015 | Tang ................... A61F 13/0246 |
| | | 602/43 |
| 2015/0119786 A1* | 4/2015 | Killeffer ............. A61M 27/006 |
| | | 604/8 |
| 2015/0209492 A1 | 7/2015 | Blott et al. |

* cited by examiner

MICRODIALYSIS DEVICE COMPRISING ATTACHMENT SHEET

CROSS-REFERENCE TO RELATED APPLICATIONS

This application is a continuation of U.S. application Ser. No. 15/755,526, filed on Feb. 26, 2018, which is a § 371 national phase of International Application No. PCT/EP2016/070634, filed on Sep. 1, 2016, which claims the benefit of Swedish Application No. 1551133-0, filed on Sep. 4, 2015, which applications are incorporated by reference herein.

TECHNICAL FIELD

The present invention relates to the field of dialysis, more particularly to the field of microdialysis devices for the monitoring of organ conditions, such as metabolic conditions, of living organs of humans and animals. More particularly, the invention relates to measuring substance concentrations on the surface of living organs for the monitoring of the condition of an organ.

BACKGROUND OF THE INVENTION

Microdialysis is a means of sampling substances from the body to help clinicians assess wellbeing or metabolic conditions by providing serial biochemical samples from a catheter which lies within the substance of an organ. Current commercial microdialysis systems are equipped for sample collection, handling, and analysis of small molecules including glucose, lactate, pyruvate and glycerol as markers or indicators of cell injury. Sample collection is based on passive diffusion through a semi-permeable material placed at the end of a catheter or a probe. Microdialysis sampling can be performed on organs which move. For example, microdialysis sampling can be used to study metabolic aspects of the beating heart. However, when a microdialysis probe is placed into the substance of a beating heart, there is always concern that the catheter position can be disturbed by the heart's contractions, as well as risk for damage to heart tissue and/or the catheter when inserting the microdialysis probe. These risks are however justified, as it has been shown that the microdialysis technique may give a more rapid and/or selective response compared to other clinical signs of ischemia (Poling, J., et al., *Myocardial metabolic monitoring with the microdialysis technique during and after open heart surgery*. Acta Anaesthesiol Scand, 2007. 51(3): p. 341-6)

When a microdialysis catheter is placed in a tissue or organ, there will unavoidably be some tissue damage. If the microdialysis method is used clinically to monitor for example a myocardial metabolic state, it is important to minimize the damage associated with probe insertion. The tissue damage caused by probe placement makes it necessary to allow an equilibration period of at least 60 to 90 minutes before reliable data can be obtained, according to manufacturer's instructions, but even the need for seven hours equilibration time has been reported (*An in vivo microdialysis characterization of the transient changes in the interstitial dialysate concentration of metabolites and cytokines in human skeletal muscle in response to insertion of a microdialysis probe*; Brian P. Carson et al, Cytokine 71 (2015) 327-333). This is done in order to allow local resorption or redistribution of fluid that may have initially accumulated surrounding the catheter at the time of insertion. If the time needed for this equilibration period could be shortened or eliminated altogether, this would allow for a more efficacious clinical application of microdialysis sampling.

Langemann introduced the microdialysis technique for studies in association with human cardiac surgery in 1996. He placed a catheter in the left ventricular wall and showed that it was possible to measure continuous changes in glucose and lactate in the myocardium.

The Swedish patent document SE434214 titled, "Dialysis Probe for Insertion in Living Tissue—has Membrane Surrounded by Stiffening Casing" describes a dialysis probe, primarily intended for insertion into biological tissues, for example brain tissue, which is comprised of a dialysis membrane and ducts for flow of the perfusion fluid over the membrane. The dialysis membrane in such a probe can be surrounded by a mounting which supports and partially reveals the membrane, and which is more rigid than the membrane. The design of the probe is not intended for organs that contract, expand or in some way move.

EP0742725B1 describes a microdialysis probe intended for insertion into tissue, having a center tube surrounded by a thin dialysis tube, which is located between two tubular fitting parts. The purpose of this arrangement is to reinforce the probe and facilitate its withdrawal without any part of the probe remaining. Despite the fragility of the dialysis tube, the distal end of the center tube from within is fixedly joined to the distal fitting part, which also has a larger diameter than the dialysis tube.

SE511932 describes a catheter that is to be inserted into a blood vessel and guided by said blood vessel. The catheter comprises a microdialysis chamber with a microdialysis membrane as part of its wall. The catheter can be connected to an external means for circulating, monitoring and analyzing a microdialysis solution passing therethrough.

WO2010068158 (MD Biomedical AB) discloses a microdialysis probe for placement on the surface of an organ. The device comprises a catheter consisting of an inlet tube and an outlet tube enclosed by an outer casing, such that perfusion solution can be circulated through the length of the catheter. The proximal end can be connected to a pump. At the distal end of the catheter a membrane is arranged. This membrane allows smaller substrates to migrate from the organ surface into the perfusion fluid. The microdialysis probe can be attached to the organ surface by using a ring at the distal end and/or by the use of an attachment girdle.

A dialysis device is subjected to considerable mechanical forces during use, due to organ movement (e.g. a beating heart or a breathing lung) and also due to the instruments and hands of the medical practitioner performing a procedure close to the probe. If the device falls off or is moved during a measurement series, the measurement procedure can give false or incorrect readings.

Hence, there is a clear need for a dialysis device that can more reliably sample changes in interstitial fluid concentrations of small molecules using dialysis sampling from a probe placed on the surface of an organ. There is also a need for more flexibility in how such a probe can be securely and safely fixated in a desired sample position.

In addition, there is also a general need for microdialysis devices which design further increases the yield of substances originating from the body fluids passing into the dialysis fluid for subsequent analysis.

In summary, there is a continuous need to create reliable, safe and efficient devices and methods for microdialysis sampling and to achieve stable methods for measuring changes, such as metabolic changes, in the condition of a body organ.

SUMMARY OF INVENTION

The above mentioned drawbacks have now been overcome or at least mitigated by the provision of a dialysis device, more particularly a microdialysis device, a kit and a method for sampling of substances from a body organ, according to the independent claims.

Hence, there is provided herein an elongated microdialysis device comprising a distal part and a proximal part, wherein the proximal part comprises an inlet and an outlet. The inlet and outlet are adapted to allow a fluid, e.g. a dialysis or perfusion fluid, to flow through the microdialysis device from the inlet through the proximal part via the distal part and back to the outlet, along substantially an entire length of the microdialysis device. The distal part of the microdialysis device is configured for temporary attachment and/or placement on a surface of a human or animal organ, and comprises a probe for sampling metabolic substances present on the surface of the organ and indicating a condition of the organ. The probe comprises an inlet channel adapted to receive fluid originating from the inlet, and an outlet channel adapted to receive fluid originating from the inlet channel.

At least part of an outer surface of the probe is adapted to be placed on the surface of an organ, where part of an outer surface of the probe comprises a semi-permeable material adapted to allow passage of substances, e.g. metabolic substances from the outside of the probe through the semi-permeable material into the fluid within said microdialysis device. Further, the device comprises an attachment sheet, which is configured to facilitate placement and/or attachment of the probe to the organ surface.

There is further provided herein a method for microdialysis sampling and/or measurement of one or more substance(s) on a surface of a human or animal organ, comprising the steps of:

a) placing and/or attaching a microdialysis device on a surface of a human or animal organ;

b) sampling and/or measuring one or more substance(s) from the surface of the organ through the semi-permeable material of said probe, and c) analyzing the results of step b).

DETAILED DESCRIPTION OF THE INVENTION

There is provided herein a device for dialysis, more particularly a device for microdialysis, configured for temporary attachment and/or placement on a surface of a human or animal organ. Advantages of using such a device are e.g. avoidance of organ damage or bleeding related to the placement of dialysis devices within solid organs using needles. Yet another advantage with dialysis measurement on the surface of an organ is the possibility to continuously follow the state, such as a metabolic state of a subject, in need thereof postoperatively. This may lead to faster diagnostics as well as minimizing complications for patients during and after surgery, such as after cardiac, abdominal or thoracic surgery. Furthermore, such a device provides the use of an advantageous microdialysis technique for perioperative monitoring during surgery, such as cardiac, abdominal or thoracic surgery.

The device presented herein further comprises an improved means of attachment of such a device for dialysis on the surface of a body organ, as well as a structure for facilitating exchange of substances between the body organ and the dialysis fluid in the form of a semi-permeable material. Herein, the semi-permeable material may also sometimes be referred to as a semi-permeable membrane.

As in customary in the art of medical devices to be used within the body, the terms "proximal" and "distal" herein refers to arrangements in relation to the user. Thus, distal parts of a device are intended to be farther away from a user than proximal parts, when the device is used as intended. Further, in the present case, the distal parts are intended to be inserted into a body, at or near a sample site, and proximal parts are intended to be outside the patient's body. Herein, the term probe refers generally to the distal end of the microdialysis device. However, it should be noted that there is no physical dividing line of the device's distal parts and its proximal parts.

In the below the device will be further described with reference to the figures. Throughout the figures the same or similar functions/items have been given the same reference signs.

Figure 1:
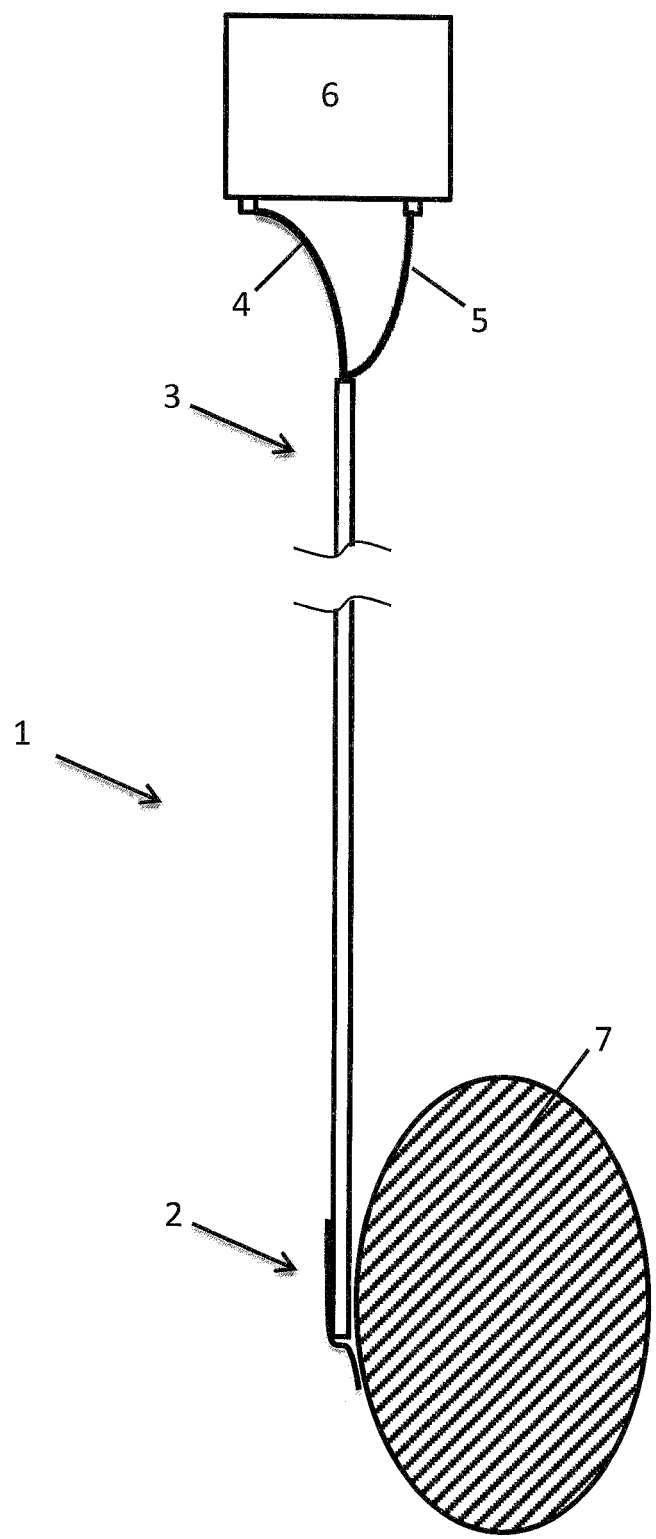
FIG. 1 shows a schematic view of a perfusion pump and a microdialysis device placed on an organ during a procedure.

Hence, a microdialysis device 1 is provided herein, having an elongated catheter-like structure, as schematically illustrated in FIG. 1. The distal end 2 of the device, shown in a cross-sectional view in FIG. 1, is adapted to be placed on the surface of an organ 7 and sample substances that follow relatively rapid changes, e.g. metabolic substances, in the organ. Details of the distal end 2 will be discussed below. Non-limiting examples of organs on which the microdialysis device can be placed for measurement are e.g. intestine, heart, lungs, liver, kidney, pancreas, urine bladder, uterus, skin, wound tissue and a foetal head during labour. These types of measurements have previously required that a catheter be placed inside the organ, i.e. within the organ tissue, to collect samples.

At the proximal end 3, i.e. away from the organ and to be arranged outside the patient's body during use, the microdialysis device 1 is provided with connection means for connecting inlet 4 and outlet 5 via tubes to a standard pump 6. When connected to a pump, a fluid, i.e. a perfusion or dialysis solution or fluid, can be pumped into and through the microdialysis device 1. The pump, tube connectors and tubing suitable for the purpose can be of any known type and are therefore not discussed further in detail.

When connected to a pump 6, fluid can flow through the microdialysis device 1 from the inlet 4 through the proximal part 3 via the distal part 2 and back to the outlet 5, along substantially an entire length of the microdialysis device 1.

The distal part 2 of the microdialysis device 1 is configured for temporary attachment and/or placement on a surface of a human or animal organ, as will be described below in detail. The distal part 2 further forms a probe 2 for sampling of substances present on the surface of the organ and indicating a condition, such as a metabolic condition, of the organ.

Figure 2A:
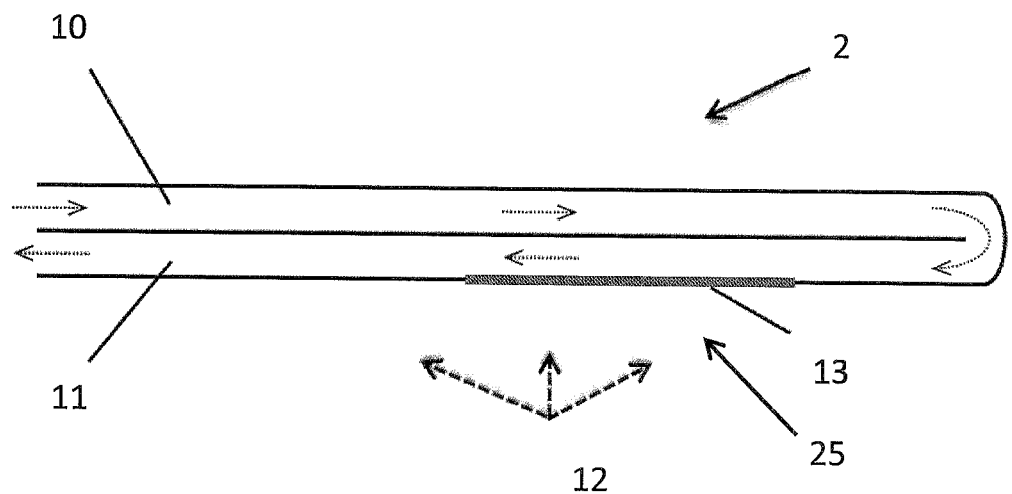
FIG. 2a shows a distal end of a microdialysis device in a longitudinal cross-sectional view.

A distal end 2 of a microdialysis device 1 is schematically illustrated in cross-sectional view in FIG. 2a. The distal end 2, forming the probe 2, comprises a catheter-like structure with two internal channels, an inlet channel 10 and an outlet channel 11. The inlet channel 10 is a continuation of a channel connected to the inlet 4 in the proximal part 3 of the device (see FIG. 1), and is thereby adapted to receive fluid originating from the inlet 4. Similarly, the outlet channel 11 is a continuation of a channel connected to the outlet 5 in the proximal part 3 of the device. The inlet channel 10 and outlet channel 11 are also connected to each other at the very distal end of the device. Thus, fluid can flow from the proximal inlet 4 through the inlet channel 10 to the outlet channel 11 and back to the proximal outlet 5. The dotted arrows within the probe in FIG. 2 show the intended direction of flow of perfusion fluid through a preferred configuration of the probe.

An outer casing as referred to herein may also be adapted to form the inlet channel 10 and the outlet 11 channel of the device 1, i.e. meaning that the inlet 10 and outlet channel 11 form an integrated unit. Herein, the outer surface of the probe 2 is sometimes also referred to as an outer casing of the probe 2.

Figure 2B:
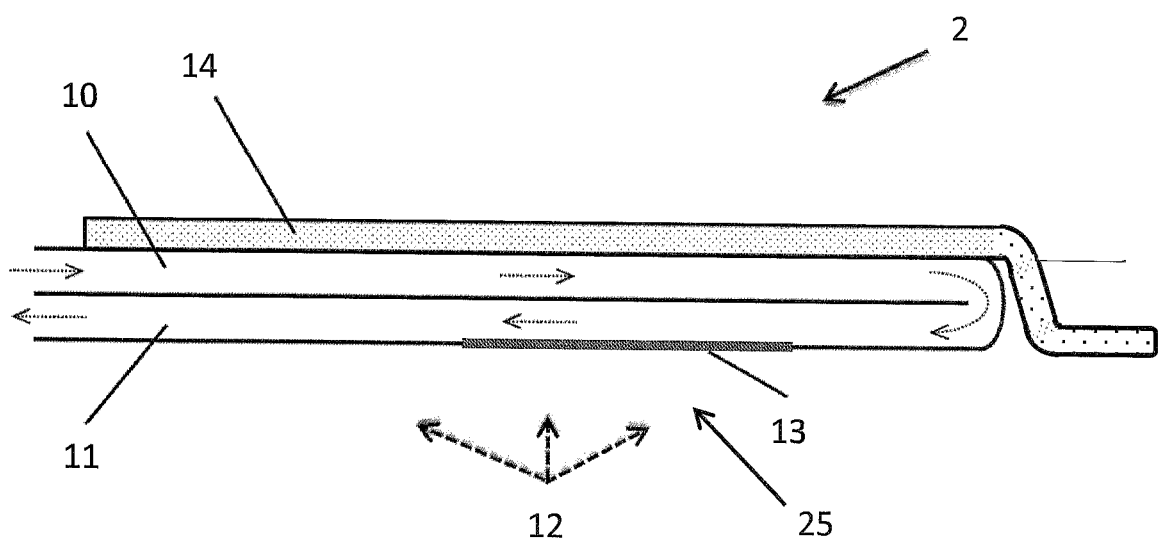
FIG. 2b shows a distal end of another microdialysis device in a longitudinal cross-sectional view.

At least part of an outer surface 12 of the probe 2 is adapted to be placed adjacent and essentially alongside the surface of an organ. In FIG. 2a, this surface is facing downwards. This part of an outer surface 12 comprises a semi-permeable material 13 which is adapted to allow passage of substances, such as metabolic substances, from the outside of the probe 2 through the semi-permeable material 13 into the fluid within said microdialysis device 1. Accordingly, the structure of the semi-permeable material 13 in FIGS. 2a and 2b is schematic illustrating that it forms an interface structure between the body organ and the perfusion fluid within the probe, facilitating diffusion of substances from the organ to the fluid flowing through the inlet and outlet channel 10, 11. Such an exchange of substances may be provided by different structural forms of the semi-permeable material 13 as further presented herein. It is further important to ensure that there is substantially no leakage of perfusion fluid out of the device, or bodily fluids or tissue into the perfusion fluid of the device. Exchange of substances between the internal perfusion fluid and the tissue or fluid outside the distal end of the device 1 should ideally only take place across the semi-permeable material 13.

The part of an outer surface 12 comprising a semi-permeable material 13 may be an integrated part of the wall of the outlet channel 11 made of the semi-permeable material 13. However, it is also conceivable that the semi-permeable material is an integrated part of the wall of the inlet channel 10. The term integrated, in this context, means that the material can either be part of the material of the inlet 11 or outlet 12 channel that has been treated to become semipermeable, such as mechanically treated, for example punctured, chemically treated, heat-treated, or subjected to similar treatment, or that a semi-permeable material has been fixed and/or attached to form a part of the outer surface 12.

The probe 2 can comprise an opening 25 in said part of an outer surface 12 wherein said semi-permeable material is arranged for sampling of substances outside said probe. As an example, an opening of a suitable shape and size can be formed in the sidewall of e.g. the outlet channel 11, and a semi-permeable material 13 arranged to substantially cover or be present in this opening. Such material can be attached in any suitable manner, such as glued, welded, taped or sewn onto the inside or outside of the device around the opening.

The side of the probe 2 comprising the semipermeable material 13 is preferably adapted to lie against an organ surface, in order to have a sufficient contact area or at least sufficiently close proximity of the semipermeable material 13 of the probe and the organ surface. Further, a sufficient contact area or at least sufficiently close proximity between the probe 2 and the organ surface may in some aspects have the advantage of avoiding evaporation of microdialysate, which can lead to artificial concentration increases. The semi-permeable material 13 may also be provided in the form of a substantially tubular-shaped perfusion tube 23, wherein at least a part of said tube is arranged within at least a part of the inlet channel 10 and/or the outlet channel 11 and that at least a part of said tube is arranged in an opening of the inlet 10 or outlet 11 channel of the device. This aspect is further described herein in connection to FIG. 4.

A distal end 2 of another aspect microdialysis device 1 is schematically illustrated in cross-sectional view in FIG. 2b. This aspect has all the features of the distal end 2 as described above. In addition the device 1 further comprises an attachment sheet 14 adapted to facilitate placement and/or attachment of the probe 2 to the organ surface. The attachment sheet 14 in this aspect is adapted to cover the probe, i.e. the distal end 2 of the microdialysis device 1, when said distal part 2 is arranged on a surface of a human or animal organ. Thus, the size of the attachment sheet 14 is of a suitable size and shape to sufficiently form a covering layer over the entire distal end 2 of the device 1, as will be described below. In FIG. 2b, showing a cross-sectional view, the attachment sheet 14 is illustrated as a schematic flat sheet, however, it is preferably a pliable sheet, preferably made of plastic or similar material, e.g. a plastic foil, suitable for providing a covering material, as well as for providing attachment means. The attachment sheet 14 is adapted to cover or enclose said probe when arranged on the surface of a human or animal organ, thereby also providing a surrounding rim 15 for the probe which may be used for attaching the probe 2 to the organ at the desired sampling site. See also FIG. 4c, which shows another view of an attachment sheet 14 covering a distal end of a probe. Notably, the part of the outer surface 12 of the probe 2 comprising the semi-permeable material is still always exposed to the desired sampling site of the organ. The probe is hence covered on the side facing away from the sampling site.

Figure 2C:
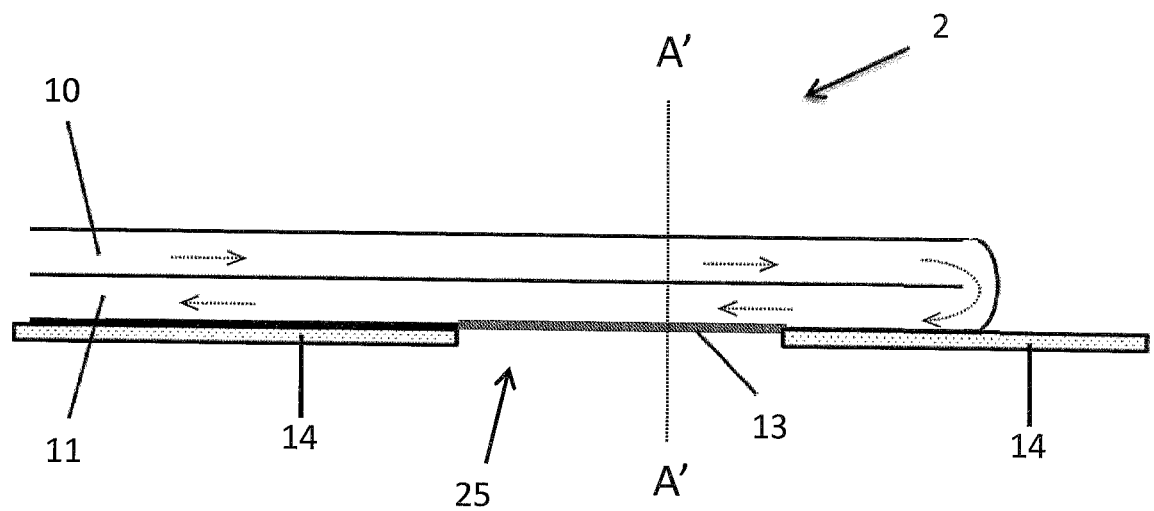
FIG. 2c shows a distal end of yet another microdialysis device in a longitudinal cross-sectional view.
Figure 2D:
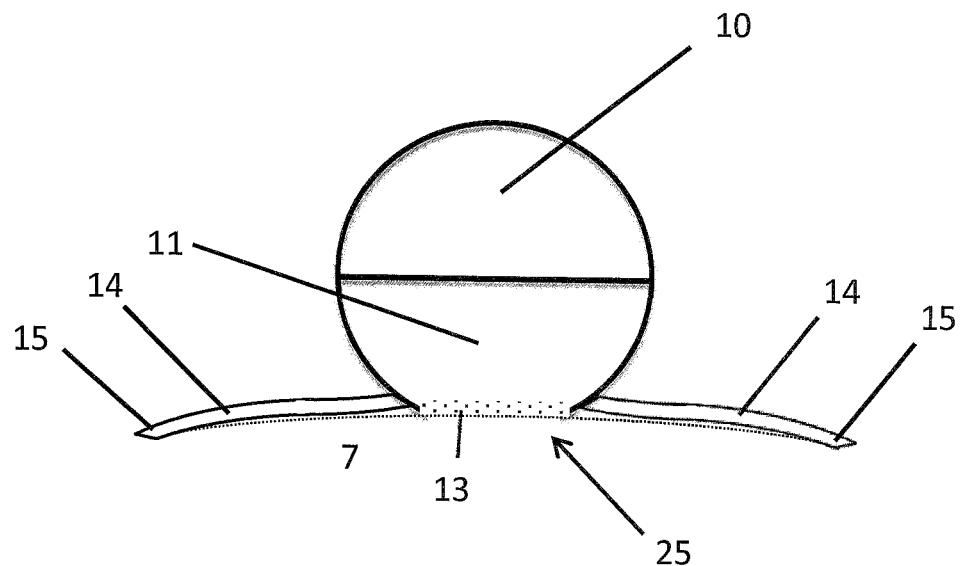
FIG. 2d shows a distal end of a microdialysis device in a cross-section perpendicular to the longitudinal axis of the device.

A distal end 2 of yet another aspect of microdialysis device 1 is schematically illustrated in two different cross-sectional views in FIGS. 2c and 2d. FIG. 2c is a cross-sectional view along a longitudinal axis of the probe, and FIG. 2d shows a cross-sectional view across the dotted line A'-A' of FIG. 2c. This configuration of the probe has all the features of the distal end 2 as described above, except that this device comprises another example of an attachment sheet 14 adapted to facilitate placement and/or attachment of the probe 2 to the organ surface. The attachment sheet 14 is adapted to be arranged against the organ surface when said distal part 2 is arranged on a surface of a human or animal organ, and comprise an opening essentially corresponding to the opening 25 in the part of the outer surface 12 where the semi-permeable material is arranged for sampling of substances outside the probe. Thus, the attachment sheet will surround the semi-permeable material of the probe and extend outwards along the organ surface in essentially all directions of the surface when in use. Thus, also in this alternative arrangement, the size of the attachment sheet 14 is of a suitable size and shape to sufficiently form a layer extending out from the probe around the entire distal end 2 of the device 1, as will be described below.

In FIG. 2c, showing a cross-sectional view in a direction along the longitudinal axis of the probe, the attachment sheet 14 is illustrated as a schematic flat sheet; however, it is preferably a pliable sheet, preferably made of plastic or similar material, e.g. a plastic foil, suitable for providing a protective material, as well as for providing attachment means. In FIG. 2d the probe 2 is shown in a cross-sectional view in a direction perpendicular to the longitudinal axis of the probe, i.e. across the dotted line A'-A' of FIG. 2c. The attachment sheet 14 is adapted to be arranged against and cover the organ surface 7 surrounding the area of sampling/dialysis via the semi-permeable material 13 of the probe when arranged on the surface of a human or animal organ, thereby also providing a surrounding rim 15 for the probe which may be used for attaching the probe 2 to the organ at the desired sampling site. Notably, the part of the outer surface 12 of the probe 2 comprising the semi-permeable material is still always exposed to the desired sampling site of the organ. The attachment sheet 14 helps enclose the sampling site of the organ surface, thus providing more effective dialysis as well as attachment means of the probe on the organ surface.

The attachment sheet 14, regardless if it is arranged to cover the entire distal end of the probe, as shown in FIG. 2b, or if it is arranged as a flattened sheet structure with an opening corresponding to the opening in the outer surface of the probe 2, i.e. surrounding the surface of the semipermeable material adapted to be arranged against the organ surface 7, as shown in FIGS. 2c and 2d, is preferably glued or welded to the probe 2, and preferably arranged such that the sheet is centred in relation to the longitudinal axis of the probe. This is schematically illustrated in FIGS. 3a-e, wherein the figure are perspective views of an attachment sheet 14 overlying a probe, as seen from the side facing away from an intended sample site of an organ surface. Dotted lines indicate the probe 2, or distal end 2 of the device, as well as the proximal extension of the device. In such probes where the attachment sheet 14 is arranged in as described for FIG. 2c, i.e. in a more flat arrangement surrounding the opening with the semi-permeable material, the same shapes are applicable. The attachment sheet 14 is further arranged to provide a surrounding rim 15 for the probe, as indicated in FIGS. 3a-e. This rim 15 may form an essentially flat structure for attachment of the probe 2 to the organ surface.

The attachment sheet 14 may have a width W equal to approximately 5 to 50 mm, such as approximately 8 mm to 40 mm, approximately 8 mm to 30 mm, approximately 8 to 20 mm, approximately 8 to 15 mm or preferably approximately 9 mm to 12 mm. The surrounding rim 15 is preferably at least 4 mm wide, such as at least 5, 6, 7, 8, 9 or 10 mm wide i.e. measures at least 4 mm from the underlying probe 2 to an outer edge of the sheet 14, to be able to securely apply sutures around the probe 2. The attachment sheet 14 may also have a surrounding rim 15 that is approximately 2 times wider than the outer diameter of the inlet tube, such as 1.5 times wider than the inlet tube, which will also be applicable to aspects of a device 1 as disclosed herein having other dimensions.

Figure 3A:
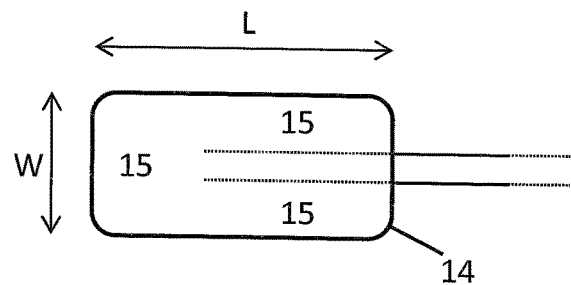
FIGS. 3a-3e show different shapes of an attachment sheet of a distal end of a microdialysis device in a perspective top view.
Figure 3B:
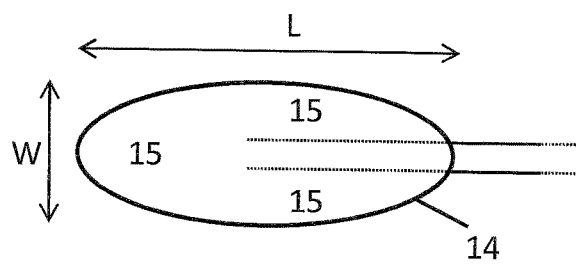
Figure 3C:
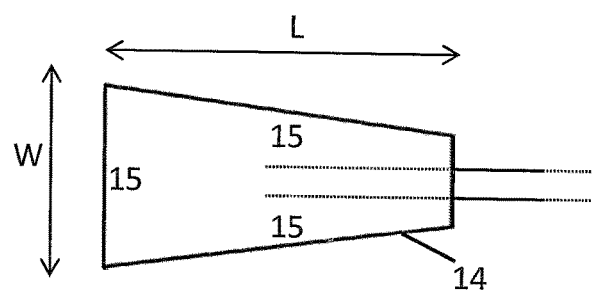
Figure 3D:
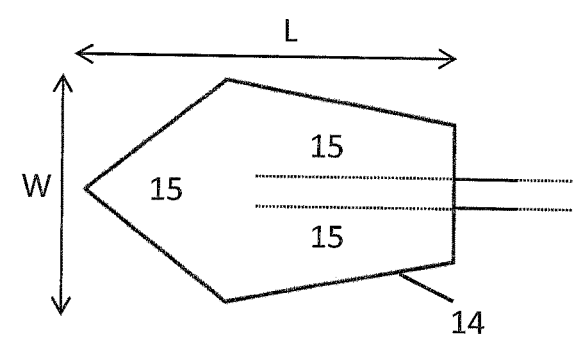
Figure 3E:
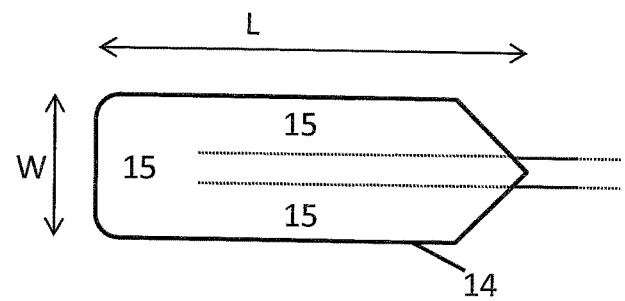

Several shapes of the attachment sheet 14 are conceivable, such as square, rectangular, elliptical, pentagonal or round shapes, as is schematically exemplified in FIGS. 3a and 3b. It can also have an elongated shape with a smaller width at one end than at the opposite end, for example such as is shown in FIG. 3c. One example is that the width at the proximal end of the attachment sheet is approximately 8 mm to 10 mm and the width at the distal end is approximately 15 mm to 30 mm. Accordingly, the attachment sheet 14 may have a width that varies along a length of said attachment sheet 14. Any other suitable shape can be used, e.g. pentagonal (FIG. 3d), and the corners can be rounded or angular. A further example of a shape is provided in FIG. 3e. Thus, any shape suitable for providing enough contact area for secure attachment to the organ is conceivable herein.

The length L of the attachment sheet 14 may be approximately 10 mm to 80 mm, such as 10 mm to 60 mm, 20 mm to 60 mm or preferably approximately 30 mm to 45 mm. One preferred example is an attachment sheet with a width of approximately 10 mm and a length of approximately 45 mm. The dimensions of the attachment sheet 14 should however preferably be such that the sampling site against the organ surface is essentially enclosed and liquid exchange with other areas minimized, and a surrounding rim 15 is formed around the probe 2. Further, depending on the type of organ on which the probe is to be placed, the size of the attachment sheet 14 should be to best suit each individual situation.

The probe 2 may be attached to the organ surface of interest by any suitable means, such as sutures, tape and/or adhesives or various types. Thus, the surrounding rim 15 may be attached with sutures or it may also have an adhesive surface (such as of a Band-Aid type).

The attachment sheet 14 is preferably of a material which can be penetrated by a needle, such that the probe can be attached to the organ by one or more sutures or staples.

The attachment sheet 14, or more particularly the surrounding rim 15, may comprise one or more pre-made holes for use in attaching the sheet to the organ surface.

As an alternative or in addition to using sutures, an adhesive layer can be applied to the side of the attachment sheet 14 facing the organ, either beforehand, similar to a Band-Aid or tape, or applied when the probe is to be attached, e.g. in the form of a surgical glue or similar.

Thus, the attachment sheet 14 facilitates attachment of the probe 2 to the organ. Furthermore, once the probe 2 has been attached to the organ, the probe, i.e. the distal end 2 of the microdialysis device 1, is prevented from moving more than minimally in relation to the organ surface, especially regarding rotational movement of the probe 2. In other words, the attachment sheet 14 contributes to holding the probe 2 in place, and especially prevents rotation of the probe. This is likely to provide for more accurate and reliable measurements, as the area of the probe where dialysis exchange occurs, i.e. where the semi-permeable material 13 is arranged, is kept in place at a specified sample site on the organ surface.

Furthermore, the structure and material of the attachment sheet 14 and the surrounding rim 15 provides for a more flexible approach when attaching sutures to secure the probe 2 to the body organ. As an example, holes for the sutures need not be pre-fabricated but can be prepared on site. Furthermore, there is a concern regarding possible positions so as to not put the patient at risk. Thus, the flexibility of the present probe 2 solves or at least mitigates this by providing for a more secure and gentle way of attachment, as well as more flexibility with regards to the positioning of the probe for each situation.

Preferably, the attachment sheet 14 is arranged, such that when attached at a sample site, it will enclose the exposed semi-permeable material against the desired sample site.

Hence, this minimizes access of surrounding fluids and/or tissue to the semi-permeable material, and ensures that dialysis only occurs in the enclosed area. Preferably, the attachment sheet 14 is, for this reason among others, made of an essentially non-permeable and/or substantially fluid-tight material. Examples of such materials are aromatic polyurethane and polytetrafluoroetylen, but they are not limited thereto.

The attachment sheet 14 can be made of an elastic material, such as Tachosil. Using a pliable elastic material minimizes any damage to the probe itself or to the organ surface, and facilitates handling and attachment.

The attachment sheet 14 can further be made of a radiopaque material, such that it is visible using e.g. X-ray or other imaging techniques. Examples of such materials may contain titanium, tungsten, barium sulphate and zirconium oxide. This is helpful if the organ of interest is visualized using such imaging techniques during or after a procedure, e.g. to ensure that the probe is secure and has not moved away from a desired sampling position. It may also be in the form of a plastic foil.

Figure 4A:
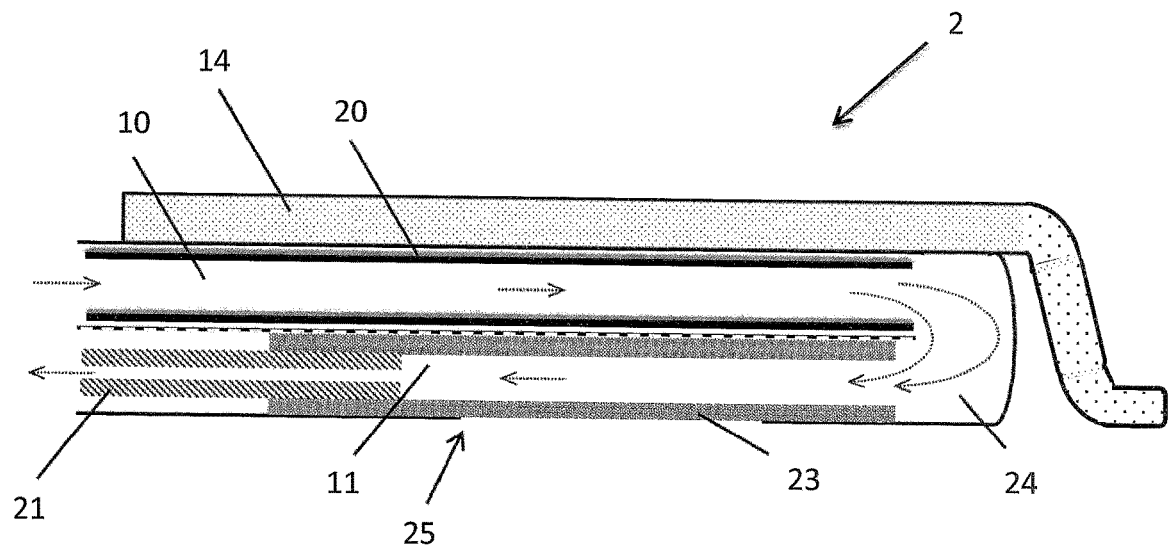
FIG. 4a-4b shows a distal end of further microdialysis devices in a longitudinal cross-sectional view.
Figure 4B:
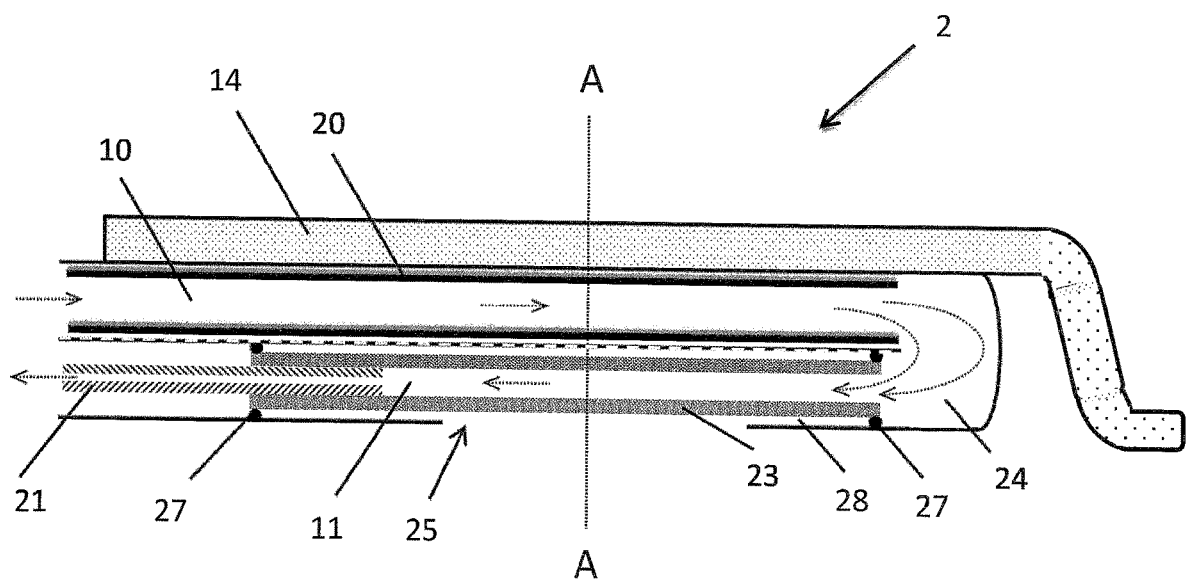

In a further aspect, illustrated in FIGS. 4a and 4b, the probe 2 may comprise an inlet channel 10 and an outlet channel 11 such as described above. The attachment sheet 14 of the probe 2 as shown in FIG. 4 is as described in connection with FIG. 2, i.e. either covering the distal end of the probe or arranged as a sheet with an opening at the semipermeable material. However, in this aspect, the inlet channel 11 further comprises an inlet tube 20. The inlet tube 20 is arranged within the inlet channel 10 and is adapted to receive fluid originating from the proximal inlet 4. In addition, the outlet channel 11 comprises an outlet tube 21, wherein the outlet tube is adapted to receive fluid originating from the inlet tube 20 via a distal chamber 24. The shape and size of the distal chamber 24 may be varied. As an alternative, the inlet tube 20 can be adapted to extend in a U-shaped distal tube part 26 as shown in FIG. 5. As a further alternative, a perfusion tube 23 can be adapted to extend in a U-shaped distal tube part instead of the inlet tube 20 (not shown). Notably the probes shown in FIG. 4 and FIG. 5 are similar in all other aspects. For instance, the attachment sheet 14 may either be arranged to cover the distal end of the probe 2, as shown in FIGS. 4a, 4b and 4c, or may be arranged on the same side as the semipermeable material, with an opening corresponding to the opening at the semi-permeable material, as shown in FIG. 4d, and corresponding to that described for FIGS. 2c and 2d above.

Figure 4C:
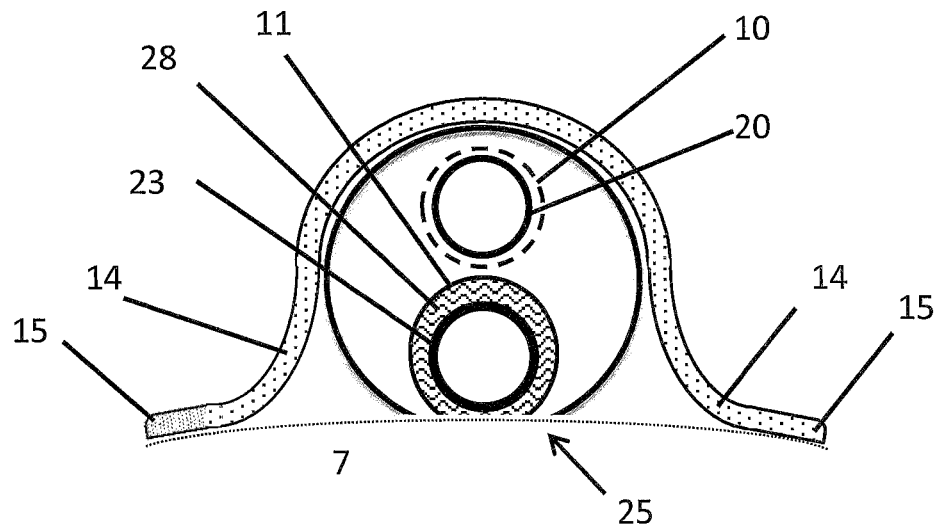
FIG. 4c shows a distal end of a microdialysis device in a cross-sectional view perpendicular to the longitudinal axis of the device.
Figure 4D:
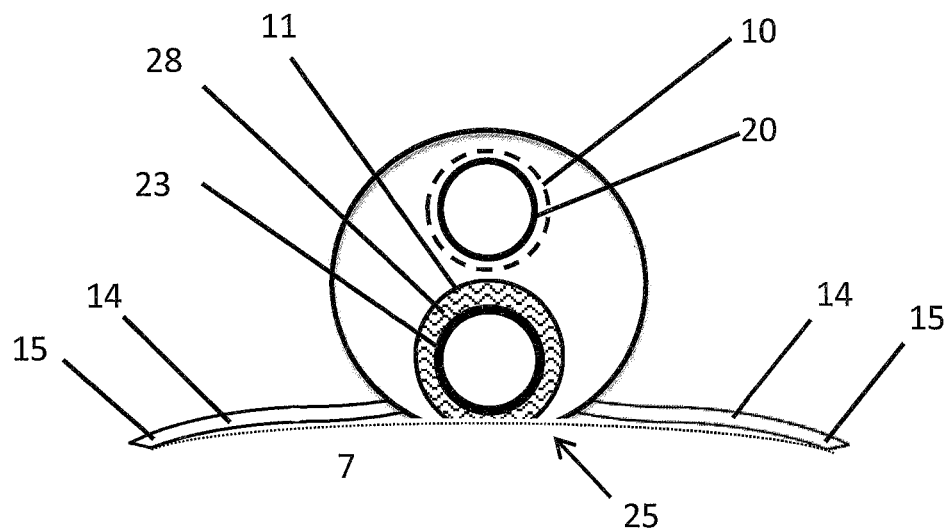
FIG. 4d shows a distal end of another microdialysis device in a cross-sectional view perpendicular to the longitudinal axis of the device.
Figure 5:
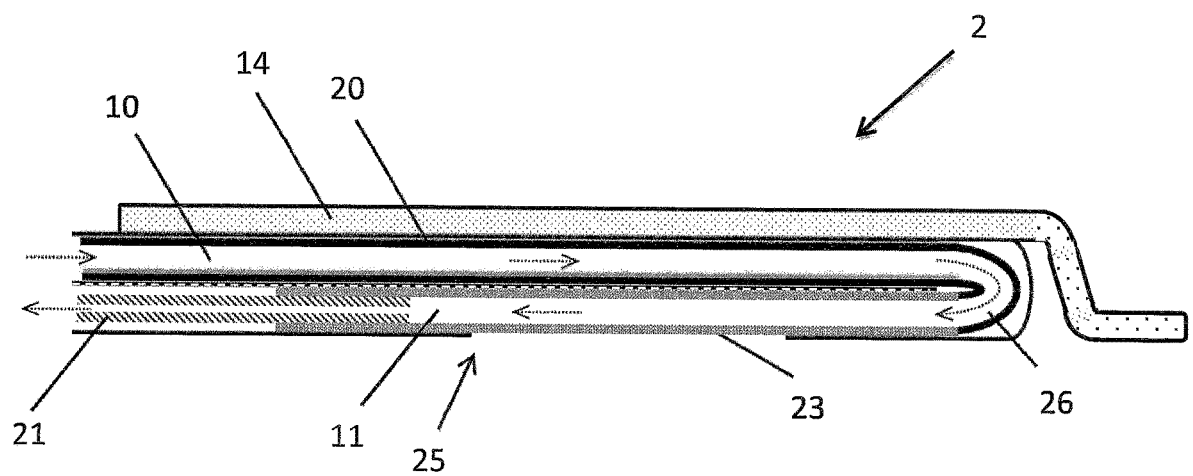
FIG. 5 shows a distal end of yet another microdialysis device in a longitudinal cross-sectional view.

As best understood from FIGS. 4c and 4d, inlet channel 10 and outlet channel 11 may be provided in the form of two separate tubes, enclosed in a larger outer tube forming the outer surface of the probe. In this outer tube an opening corresponding to opening 25 is provided, as best seen in FIGS. 4a and 4b. Further, the attachment sheet 14 is preferably attached to this outer tube, as seen in FIGS. 4a and 4b, as well as in FIGS. 4c and 4d.

In an alternative configuration, the inlet channel 10 and outlet channel 11 may be provided as two separate channels in a solid cylindrical elongated device, with an opening 25 provided to give access to one of the channels via the semipermeable material. In a further alternative configuration, the inlet channel 10 and outlet channel 11 may be provided as two separate channels in a larger outer tube, e.g. similar to as seen in FIG. 2d (i.e. as two semi-circular halves of a larger tube), wherein an inlet tube 20 may be arranged within the inlet channel 10, and/or an outlet tube 21 may be arranged within the outlet channel 11 (not shown).

As in the previous aspects, in the probes illustrated in FIGS. 4a-4d, a semipermeable material 13 is arranged such that small substances can be exchanged through dialysis between a sampling site on an organ and internally flowing perfusion fluid in the outlet channel. However, in these aspects the semipermeable material 13 is provided in the form of a substantially tubular shaped perfusion tube 23 formed of suitable semipermeable material 13.

This perfusion tube 23 is arranged within at least part of the outlet channel 11 and/or the inlet channel 10, and said perfusion tube 23 is arranged to allow passage of substances from the outside of said probe 2 through said semi-permeable material 13, and wherein said perfusion tube 13 may be partly threaded over the distal end of the outlet tube 21, in order to provide a secure connection wherein fluid can flow through. However, other attachment means can be used, such as glue or other adhesives, to attach the perfusion tube 23 to the outlet tube 21.

The perfusion tube 23 is further arranged such that it is exposed to the surrounding volume of the organ, for sampling of substances, through an opening 25 in an outer channel 11 of the probe 2. The perfusion tube 13 may be arranged so that said fluid can flow from said inlet channel 10 via said perfusion tube 23 and to said outlet tube 21.

In the probe 2 shown in FIG. 4a, the perfusion tube is arranged such that its outer surface lies up against the inner surface of the outlet channel 11. Thus, the perfusion tube 23 is partly arranged within the opening 25, and will seal tightly against any leakage of perfusion fluid. Alternatively, the perfusion tube can be glued or otherwise attached against the opening 25.

In the probe 2 of FIG. 4b a variation of the arrangement of the perfusion tube 23 within the opening 25 is shown. Here, the perfusion tube 23 is slightly movable within the probe 2 and the positioning thereof rendering it possible for the body fluid of the surrounding volume to create a liquid column around the perfusion tube 23 within the outlet channel 11. Hence, as shown in FIG. 4b there is a space 28 formed around the perfusion tube 23 allowing for body liquids to enter the probe 2 and thereby surround the perfusion tube 23. This space 28 is created by the attachment 27 of the perfusion tube 23 to the inner walls of the outlet channel 11, and/or the outer wall of the inlet tube 20 at one end, on the distal side of the opening 25, and the attachment 27 of the proximal end of the perfusion tube 23 and optionally of the outlet tube 21 at the other end. Thereby, an environment facilitating exchange of substances between the organ and the perfusion liquid is provided. This is also illustrated in FIG. 4c, which is a cross-sectional view as seen across the line A-A in FIG. 4b. The probe is here arranged with the sample opening 25 against the surface of an organ 7, and the probe is attached using an attachment sheet 14 as described above. In FIG. 4c it is clearly seen that the perfusion tube 23 is arranged within the outlet channel 11 such that a space 28 is formed, where bodily fluid can enter, and the fluid can thereby surround the perfusion tube 23 within the outlet channel 11. This allows for a larger surface for dialysis, i.e. exchange of molecules between the bodily fluid outside the perfusion tube 23 and the perfusion fluid inside the perfusion tube 23.

FIG. 4d shows a similar probe as that of FIG. 4a, 4b, and 4c, wherein the only difference is that the attachment sheet 14 is arranged on the side of the semipermeable material, i.e. the opening 25, and provided with an opening corresponding to the opening 25, similar to the probe shown in FIGS. 2c and 2d above. An advantage of this arrangement is that, when the probe 2 is placed against an organ surface 7, the sampling site is tightly enclosed against the opening 25, and liquid exchange with other areas minimized. As can be seen when comparing FIG. 4c with FIG. 4d, the sampling volume is substantially smaller, allowing for more effective dialysis. Further, arranging the attachment sheet 14 in this manner provides for easier attachment, as the sheet is in a flat configuration also before placement on the organ. In addition, it is the experience of the inventor that it is more intuitive for a user to place the probe correctly when in this configuration, in that the probe is placed against the organ surface with the flatter side towards the surface.

As seen in e.g. FIGS. 4a and 4b, the distal chamber 24 is positioned in the distal end of the probe 2 and created by another cavity formed between the perfusion tube 23 and the inlet tube 20 when the perfusion tube 23 has been secured to the inner walls of the outlet channel 11, such as by gluing. Securing the perfusion tube 23 to the inner wall ensures that no body fluids enter the perfusion fluid from the organ on which the probe 2 is attached. The other end of the perfusion tube 23 is attached to the outlet tube 21, such as previously described herein, to secure that virtually no leakage occurs at that end. The formation of the space 28 illustrated in FIGS. 4b, 4c and 4d is also applicable to the aspect shown in FIG. 5, although it is not shown.

Also supported by the present disclosure is an aspect of a device 1 as presented in FIGS. 4a, 4b, 4c or 4d and 5 but wherein the attachment sheet 14 does not form part of the device 1.

Figure 6:
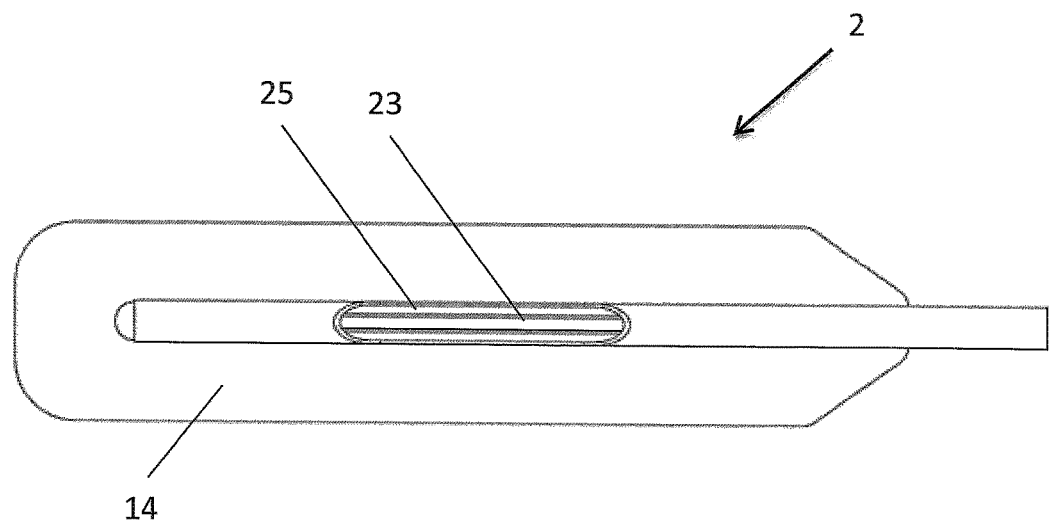
FIG. 6 shows a perspective view of a distal end of a microdialysis device seen from the side of the device adapted to face an organ.

In FIG. 6 it is shown the side of the probe 2 that is facing the organ of an aspect of the device 1. Therein, it is shown the perfusion tube 23 in the centre of the opening 25 of the probe that is exposed to the surrounding environment.

As an alternative to or variation of the above arrangements, a semi-permeable material 13 can be arranged in different manners in relation to an opening 25 in a sidewall of a probe 2. Such semi-permeable material 13 may cover the entire opening, to avoid any leakage of fluid in either direction. However, the semi-permeable material 13 can be attached at or close to the periphery of an opening in an outside wall of a probe 2, such that it covers the opening, either on the inside, outside or within (i.e. in line with) the opening.

The semi-permeable material 13 can comprise polymer compositions, such as Polyethylene (PE), Polypropylene (PP), fluoropolymers like Polytetrafluoroethylene (PTFE), Polycarbonate (PC), PAES (polyarylethersulfone), Mixed Cellulose Ester (ME), Polysulfone (PS) and Polyethersulphone (PES) or inorganic materials based on metals like alumina or zirconium or composites of materials providing a microporous structure. The material may have been surface treated to enhance wettability, selectivity and transport properties for a particular application. In all aspects, the semi-permeable material 13 can have a thickness of approximately 0.01 to 0.09 mm. When arranged in the form of a perfusion tube, the inner diameter can be approximately 0.3 to 1.6 mm, more preferably 0.4 to 0.5 mm.

An inlet tube 20 may have an inner diameter of approximately 0.3 to 1.5 mm, such as about 0.5 to 0.6 mm. This provides for a sufficient flow rate through the probe.

An outlet tube 21, arranged such that fluid can flow through it after dialysis has occurred, as described in connection with FIGS. 4a, 4b, 4c, 4d and 5, preferably has an inner diameter of approximately 0.1 to 0.5 mm, such as about 0.15 mm. The inner diameter of the outlet tube 21 is such that the delay in the liquid flow therefrom is as short as possible but that reverse flow of the liquid is avoided.

The inlet tube 20, outlet tube 21 and/or the outer casing of the microdialysis device may comprise a polymer material such as for example polyurethane, polyamide, or polyimide. Other materials than the ones mentioned, that are suitable for the purpose, may of course also be used for the probe and its parts.

It is moreover feasible to arrange the inlet and outlet channels in all described probes herein in the reversed configuration, i.e. such that the inlet channel is arranged closest to the side adapted to be placed against an organ surface, and the semipermeable material arranged in the wall of the inlet channel. It is thus also conceivable that the semi-permeable material 13 can be arranged in a sidewall of an inlet channel 10, in all the above described arrangements. This reverses the flow direction of the liquid, such that the dialysis liquid will flow first past the semipermeable material where dialysis occurs, and thereafter through the distal end of the probe, and back through the outlet channel.

As seen in FIGS. 4a and 4b, the two channels 10, 11 of a probe 2 can be connected to each other at the distal end of the device 2 via a distal chamber 24. The provision of such a chamber 24 may add further advantages to the probe 2 by facilitating liquid turbulence which may enhance exchange of substances between the body fluids and the perfusion liquid in the probe 2. In a preferred aspect, the probe is arranged with such a distal chamber 24 and with the flow direction as shown in the figures, and thus the semi-permeable material arranged in the outlet channel. Such a configuration most likely causes turbulence in the perfusion liquid, due to the distal chamber 24, immediately prior to microdialysis over the semi-permeable material, which provides for optimal results in the dialysis process.

Using any of the above described microdialysis devices, it is possible to sample and measure one or more substance(s) on the surface of a human or animal organ, such as metabolic substances, using the following method. Thus, a user may first place and/or attach a probe of a device as disclosed herein to an organ surface as described above, using the described attachment sheet 14. Thereafter, sampling and/or measuring one or more substances from the surface of the organ through the semi-permeable material 13 of said device 1 is performed, followed by analysing the results of the previous step(s). The method may indicate the metabolic condition of an organ.

More specifically, when a perfusion fluid is pumped through the device 1 as described, one or more substance(s), such as metabolic substances, passes through the semipermeable material 13 from the surface of the organ, which is arranged adjacent to the outside surface of the probe 2 at the semi-permeable material 13, to the fluid inside the probe. At the proximal end of the device 1, in connection to the perfusion pump, the circulated fluid is collected and the substances can be measured and/or analysed using commonly known methods.

Examples of substances that can be analysed in a method herein are one or several of the following: glucose, lactate, pyruvate, glycerol, amino acids, radioactively labelled molecules, cytokines, alcohols and drug metabolites, but are not limited thereto. The described method can be used to measure indications of metabolic conditions of an organ.

There is also provided herein a kit for dialysis sampling, such as microdialysis sampling, said kit comprising a dialysis device as disclosed herein, tubes for attachment to an instrument for analysis, and optionally an analysis instrument, instructions for use and/or a pump.

The invention claimed is:

1. An elongated microdialysis device (1) comprising a distal part (2) and a proximal part (3), said proximal part (3) comprising an inlet (4) and an outlet (5), said inlet (4) and outlet (5) adapted to allow a fluid to flow through said microdialysis device (1) from said inlet (4) through said proximal part (3) via said distal part (2) and back to said outlet (5), along substantially an entire length of said microdialysis device (1),
   wherein said distal part (2) of said microdialysis device (1) is configured for temporary attachment and/or placement on a surface of a human or animal organ, and said distal part (2) comprises a probe (2) for sampling substances present on said surface of said organ and indicating a condition of said organ, said probe comprising
   an inlet channel (10) adapted to receive fluid originating from said inlet (4),
   an outlet channel (11) adapted to receive fluid originating from said inlet channel (10),
   wherein at least part of an outer surface (12) of said probe (2) is adapted to be placed on said surface of an organ, said part of the outer surface of said probe comprising a semi-permeable material (13, 23) adapted to allow passage of substances from the outside of said probe through said semi-permeable material (13, 23) into said fluid within said microdialysis device (1), characterized in that said device further comprises an attachment sheet (14), said attachment sheet (14) being configured to facilitate placement and/or attachment of said probe (2) to said organ surface, the side of the probe (2) comprising the semi-permeable material (13) being adapted to lie against said organ surface,
   wherein said attachment sheet is adapted to be arranged essentially flat against the organ surface when said distal part (2) is arranged on a surface of a human or animal organ, said attachment sheet (14) comprising an opening essentially corresponding to said part of the outer surface comprising the semi-permeable material (13, 23), and
   wherein said attachment sheet is made of a substantially fluid-tight material and blocks access to said semi-permeable material by surrounding fluids when the probe is attached to a surface by the attachment sheet.

2. The device according to claim 1, wherein said inlet channel (10) comprises an inlet tube (20), said inlet tube (20) being adapted to receive fluid originating from said inlet (4), and/or wherein said outlet channel (11) comprises an outlet tube (21), said outlet tube (21) being adapted to receive fluid originating from said inlet tube (20).

3. The device according to claim 1, wherein said probe (2) comprises an opening (25) in said part of an outer surface (12) and wherein said semi-permeable material (13, 23) is arranged in said opening for sampling of substances outside said probe.

4. The device according to claim 1, wherein said semi-permeable material (13, 23) is provided in the form of a substantially tubular shaped perfusion tube (23) arranged within at least part of the inlet channel (10) and/or the outlet channel (11), and that at least part of said perfusion tube (23) is arranged to allow passage of metabolic substances from the outside of said probe through said semi-permeable material (13, 23) into said fluid within said inlet channel (10) or outlet channel (11) of said device.

5. The device according to claim 1, wherein said attachment sheet (14) is adapted to provide a surrounding rim (15) for said probe, said rim (15) having an essentially flat structure for attachment of said probe to said organ surface.

6. The device according to claim 1, wherein said attachment sheet (14) comprises an elastic material or a radiopaque material, or is in the form of a plastic foil.

7. The device according to claim 1, wherein said attachment sheet (14) has a square, rectangular, elliptical, pentagonal or round shape.

8. The device according to claim 1, wherein a width of said attachment sheet (14) is equal to approximately 8 mm to 40 mm, such as approximately 8 mm to 15 mm.

9. The device according to claim 1, wherein a length of said attachment sheet (14) is equal to approximately 10 mm to 80 mm, such as approximately 30 mm to 45 mm.

10. The device according to claim 1, wherein a width of said attachment sheet (14) varies along a length of said attachment sheet.

11. The device according to claim 3, wherein said opening (25) is arranged in a side wall of said outlet channel (11).

12. The device according to claim 4, wherein said at least part of said perfusion tube (23) is arranged in said opening (25) for sampling of substances, such as metabolic substances.

13. The device according to claim 4, wherein said perfusion tube (23) is arranged such that said fluid can flow from said inlet channel (10), via said perfusion tube (23) and to said outlet tube (21).

14. The device according to claim 4, wherein said perfusion tube (23) has an outer diameter of approximately 0.3 mm to 1.6 mm.

15. A kit comprising a microdialysis device according to claim 1, said kit further comprising tubes for attachment to an analysis instrument, and optionally an analysis instrument, instructions for use and/or a pump.

16. A method for microdialysis sampling and/or measurement one or more substance(s) on the surface of a human or animal organ comprising the steps of:
   a) placing and/or attaching a probe (2) of a microdialysis device (1) according to claim 1 on a surface of a human or animal organ;
   b) sampling and/or measuring one or more substance(s) from the surface of the organ through the semi-permeable material (13, 23) of said probe (2), and
   c) analyzing the results of step b).

* * * * *